United States Patent
Crabtree et al.

(10) Patent No.: US 10,789,264 B2
(45) Date of Patent: Sep. 29, 2020

(54) AUTOMATING CONFIGURATION OF OPERATIONAL DATA PIPELINES FOR EXTRACTION, TRANSFORMATION AND LOAD

(71) Applicant: International Business Machines Corporation, Armonk, NY (US)

(72) Inventors: Christopher L. Crabtree, Waite Hill, OH (US); Anyi Li, Rocky River, OH (US); Scott J. McCallen, Stow, OH (US); Kaveh Noorbakhsh, Mayfield Heights, OH (US); Patrick J. Sullivan, University Heights, OH (US); Matthew J. Wollerman, II, Milwaukee, WI (US)

(73) Assignee: International Business Machines Corporation, Armonk, NY (US)

( * ) Notice: Subject to any disclaimer, the term of this patent is extended or adjusted under 35 U.S.C. 154(b) by 313 days.

(21) Appl. No.: 15/001,643

(22) Filed: Jan. 20, 2016

(65) Prior Publication Data
US 2017/0206255 A1    Jul. 20, 2017

(51) Int. Cl.
*G06F 16/25*   (2019.01)
*G16H 40/63*   (2018.01)
(Continued)

(52) U.S. Cl.
CPC .......... *G06F 16/254* (2019.01); *G16H 10/60* (2018.01); *G16H 40/20* (2018.01); *G16H 40/63* (2018.01); *G16H 40/67* (2018.01)

(58) Field of Classification Search
CPC .. G06F 17/30575; G06F 19/321; G06F 21/60; G06F 21/214; G06F 16/21; G06F 16/285; G06F 16/254
See application file for complete search history.

(56) References Cited

U.S. PATENT DOCUMENTS

2008/0279562 A1   11/2008   Naoe et al.
2009/0327343 A1   12/2009   McCormack et al.
(Continued)

FOREIGN PATENT DOCUMENTS

WO   2015128612 A1   9/2015

OTHER PUBLICATIONS

"The Explorys Platform", IBM Watson Health, Solution Brief, Produced in the United States of America, Nov. 2015, 4 pages.
(Continued)

*Primary Examiner* — Mariela Reyes
*Assistant Examiner* — Courtney Harmon
(74) *Attorney, Agent, or Firm* — Will Stock; SVL IPLaw Edell, Shapiro & Finnan, LLC

(57) ABSTRACT

A method, a processing device and a computer program product are provided. Based on parameters pertaining to a data source, a first processing device may determine whether a data source is a known data source. If the data source is determined to be the known data source, then the first processing device sends respective configuration information to multiple processing devices. The respective configuration information being based on configuration information from a previous integration and configuring the multiple processing devices as an operational data pipeline to extract data from the known data source, transform the extracted data to a first data model employed by a data system, and load the transformed data into the data system.

13 Claims, 8 Drawing Sheets

(51) Int. Cl.
*G16H 10/60* (2018.01)
*G16H 40/67* (2018.01)
*G16H 40/20* (2018.01)

(56) References Cited

U.S. PATENT DOCUMENTS

| | | | |
|---|---|---|---|
| 2013/0173539 A1* | 7/2013 | Gilder | G06F 17/30578 707/622 |
| 2013/0179982 A1* | 7/2013 | Bridges | H04L 63/0823 726/26 |
| 2013/0191185 A1* | 7/2013 | Galvin | G06Q 10/10 705/7.37 |
| 2014/0032240 A1 | 1/2014 | Lougheed et al. | |
| 2014/0180982 A1* | 6/2014 | Murphy | G06N 5/022 706/14 |
| 2014/0188840 A1* | 7/2014 | Agarwal | G06F 17/30321 707/711 |
| 2014/0257852 A1* | 9/2014 | Walker | G06F 19/3456 705/3 |
| 2014/0280142 A1* | 9/2014 | Wasson | G06F 16/2465 707/737 |
| 2015/0169717 A1* | 6/2015 | Wang | G06Q 50/20 707/618 |
| 2016/0127465 A1* | 5/2016 | Barstow | G06F 16/273 707/620 |
| 2016/0180030 A1 | 6/2016 | Gunawardena et al. | |
| 2016/0210427 A1* | 7/2016 | Mynhier | G16H 50/20 |

OTHER PUBLICATIONS

List of IBM Patents or Patent Applications Treated as Related, Jun. 2017, 1 page.

* cited by examiner

FIG. 8

```
- :source_data: ALLERGY_MH_SH_HABITS_HM_JOINED
  :extract_type: VIEW
  :format: AVRO
  :publish_env: prod
  :publish_strategy: PATIENT
  :publish_xml_path: ALLSCRIPTS_PRO/publishers/allergy_mh_sh_habits_hm.rb
  :publish_properties_path: "#{path}/publisher.yaml"
  :enabled: N
- :source_data: DIAGNOSES_PROBLEMLIST_JOINED
  :extract_type: VIEW
  :format: AVRO
  :publish_env: prod
  :publish_strategy: PATIENT
  :publish_xml_path: ALLSCRIPTS_PRO/publishers/diagnoses_problemlist.rb
  :publish_properties_path: "#{path}/publisher.yaml"
  :enabled: N
- :source_data: DRUG_ORDERS_JOINED
  :extract_type: VIEW
  :format: AVRO
  :publish_env: prod
  :publish_strategy: PATIENT
  :publish_xml_path: ALLSCRIPTS_PRO/publishers/drug.rb
  :publish_properties_path: "#{path}/publisher.yaml"
  :enabled: N
- :source_data: ENCOUNTER_JOINED
  :extract_type: VIEW
  :format: AVRO
  :publish_env: prod
  :publish_strategy: PATIENT
  :publish_xml_path: ALLSCRIPTS_PRO/publishers/encounter.rb
  :publish_properties_path: "#{path}/publisher.yaml"
  :enabled: N
- :source_data: HABIT_JOINED
  :extract_type: VIEW
  :format: AVRO
  :publish_env: prod
  :publish_strategy: PATIENT
  :publish_xml_path: ALLSCRIPTS_PRO/publishers/habits.rb
  :publish_properties_path: "#{path}/publisher.yaml"
  :enabled: N
- :source_data: HPSITE.ALL_HXDIAGNOSIS_ATTRIBUTES_VIEW
  :extract_type: FULL
  :format: AVRO
  :publish_env: prod
  :publish_strategy: JOIN
  :publish_xml_path: ALLSCRIPTS_PRO/record_joins/habits.pig
  :enabled: Y
  :publish_properties_path: ALLSCRIPTS_PRO/record_joins/habits.properties
```

AUTOMATING CONFIGURATION OF OPERATIONAL DATA PIPELINES FOR EXTRACTION, TRANSFORMATION AND LOAD

BACKGROUND

1. Technical Field

Present invention embodiments relate to automatic configuring for a data extraction, transformation and load system, and more specifically, to automatically configuring multiple components of a data pipeline for extraction, transformation and load.

2. Discussion of the Related Art

A system includes a gateway coupled to one or more clinical/operational data sources that provide various types of medical information including, but not limited to, electronic health records, claims, a lab feed, Health Level 7 (HL7) conforming files, and patient satisfaction surveys. Currently, all configurations for processing devices in a data pipeline are manually set up for connection, extraction, transformation and loading for each new customer. Developing manual configurations can be time-consuming and error-prone.

SUMMARY

A machine-implemented method, a computer program product, and a processing device are provided for integrating source data into a data system. A first processing device may determine, based on parameters pertaining to a data source, whether the data source is a known data source. When the data source is determined to be the known data source, the first processing device may send, to multiple processing devices of an operational data pipeline having services, framework and software infrastructure at each of the processing devices, configuration information, which is based on configuration information from a previous integration for the determined known data source. The respective configuration information configuring the multiple processing devices to extract data from the known data source, transform the extracted data to a first data model employed by the data system, and load the transformed data into the data system.

BRIEF DESCRIPTION OF THE DRAWINGS

Generally, like reference numerals in the various figures are utilized to designate like components.

FIG. 8 shows an example input to a configuration processing device to be used by the configuration processing device to determine how to configure publishers in a staging relational database management system and extractors on a data gateway.

DETAILED DESCRIPTION

Various embodiments automatically configure components of an operational data pipeline system when a pattern pertaining to a source file is known, thereby saving time and reducing occurrences of configuration errors.

Figure 1:
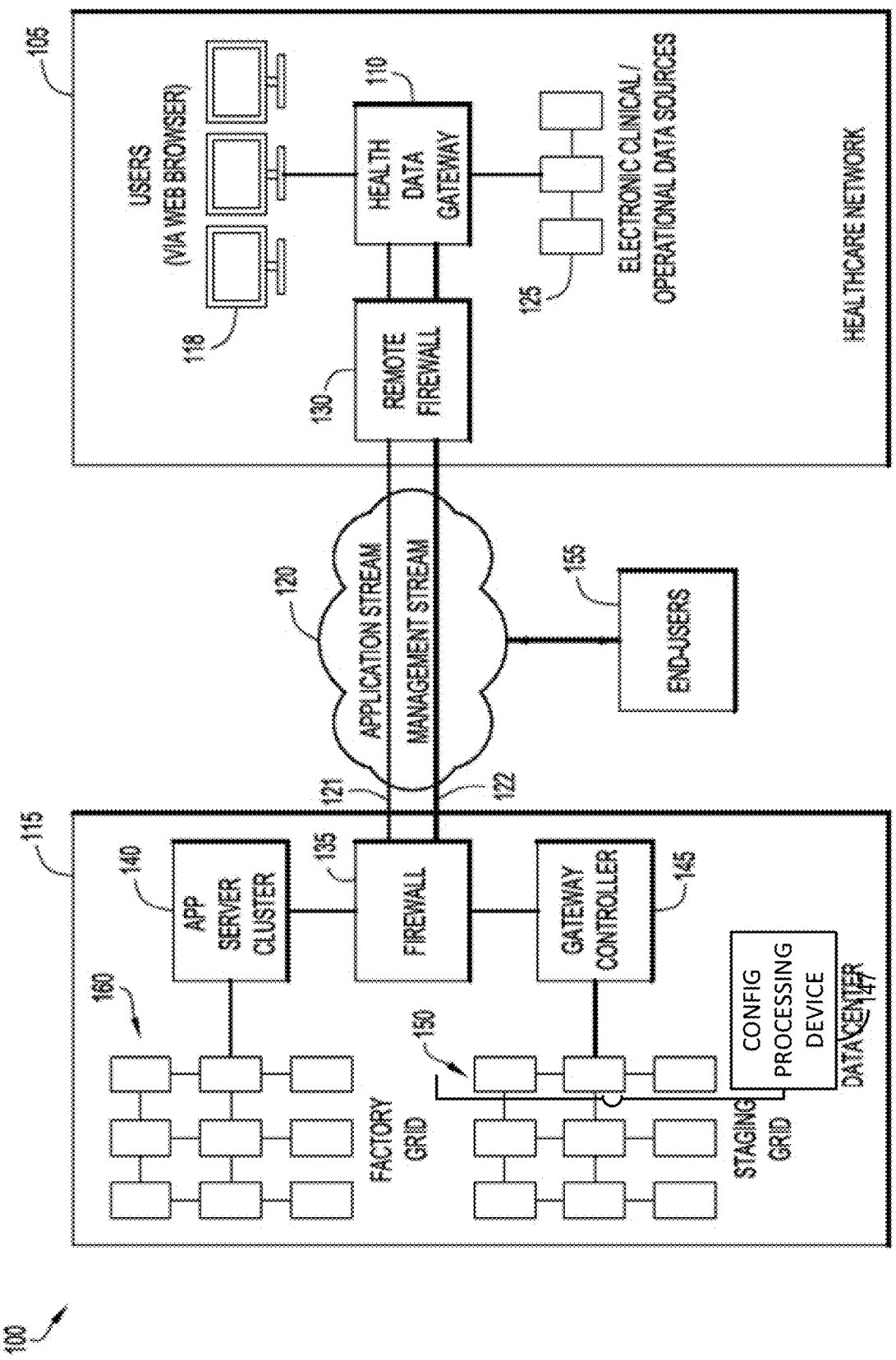
FIG. 1 is a diagrammatic illustration of an example computing environment according to an embodiment of the present invention.

An example computing environment for use with present invention embodiments is illustrated in FIG. 1. Computing environment 100 includes a healthcare network 105 in communication with a data center 115 over a communications network 120 (e.g., providing a secure virtual private network (VPN)). The communications over network 120 preferably occur between a firewall 130 of healthcare network 105 and a firewall 135 of data center 115. The communications over network 120 may include an application stream 121 pertaining to communications for applications and a management stream 122 pertaining to communications for managing the data. The network may be implemented by any number of any suitable communications media (e.g., wide area network (WAN), local area network (LAN), Internet, Intranet, etc.). Alternatively, healthcare network 105 and data center 115 may be local to each other, and communicate via any appropriate local communication medium (e.g., local area network (LAN), hardwire, wireless link, Intranet, etc.).

Healthcare network 105 includes a health data gateway 110 coupled to end-user systems 118 and one or more clinical/operational data sources 125 providing various medical information (e.g., electronic health records (EHR), records from a claims system, lab feed, various data sources implementing the HL7 standard, patient satisfaction survey, etc.) stored according to a source data model.

Data center 115 includes an application server cluster 140, a gateway controller 145, a staging grid 150, and a factory grid 160. Health data gateway 110 of healthcare network 105 is configured to acquire data from data sources 125 and transmit the acquired data to gateway controller 145 of data center 115. The gateway controller receives the incoming data from the communications network and processes that data to staging grid 150. The staging and factory grids each include a cluster of computer systems to store data and perform parallel processing. By way of example, the staging and factory grids each employ a HADOOP cluster with a HADOOP distributed file system (HDFS).

Staging grid 150 inspects and publishes the data to factory grid 160 in accordance with a data model employed by the factory grid. Factory grid 160 includes various engines to perform desired analytics on the data based on queries received from end-user systems 118 and other end-user systems 155 accessing data center 115 over network 120. The queries are handled in conjunction with application server cluster 140 to produce desired results.

A configuration processing device 147, which may be co-located at data center 115, may determine whether a data source for a new customer is a known data source from a previous integration. If the data source is determined to be a known data source, configuration processing device 147 may retrieve configuration information from a data repository (not shown) and may configure each of health data gateway 110, gateway controller 145, staging grid 150 and factory grid 160, all of which make up an operational pipeline.

Figure 2:
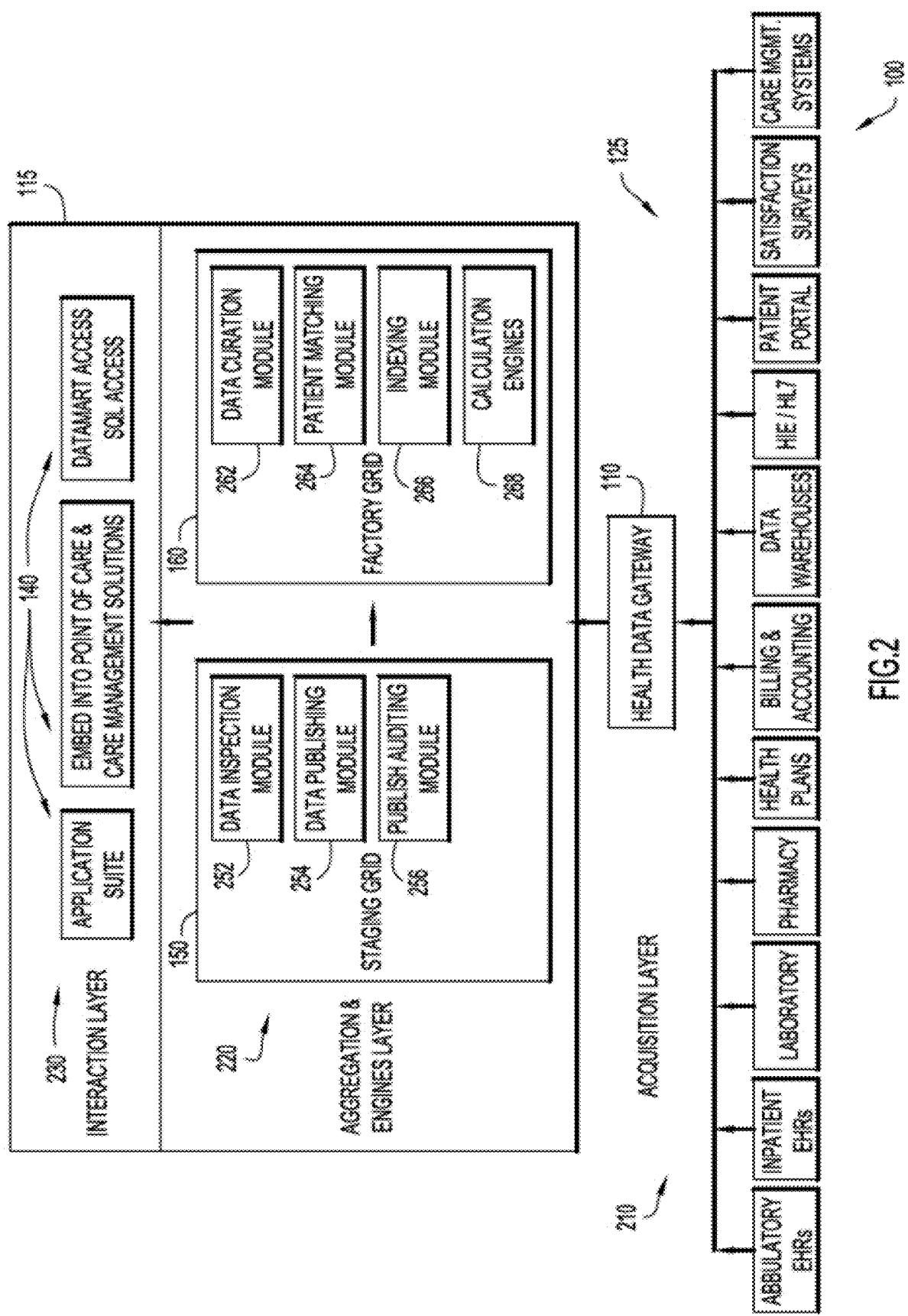
FIG. 2 is a diagrammatic illustration of the data center of the computing environment of FIG. 1 according to an embodiment of the present invention.

Referring to FIG. 2, health data gateway 110 of one or more healthcare networks is configured to acquire data from data sources 125 of those healthcare networks (e.g., ambulatory electronic health records (EHR), inpatient electronic health records (EHR), laboratory data, pharmacy data, health plan data, billing and accounting data, data warehouses, health information exchange (HIE)/HL7 data, patient portal, satisfaction surveys, care management systems, etc.) and transmit the acquired data to gateway controller 145 of data center 115 as described above. The healthcare networks and/or data sources 125 form an acquisition layer 210 providing data to data center 115 via health data gateway 110.

Gateway controller 145 receives the incoming data from communications network 120 and processes that data to staging grid 150 employing data models of the source systems. Staging grid 150 includes a data inspection module 252, a data publishing module 254, and a publish auditing module 256 to inspect, publish, and audit the data to factory grid 160 in accordance with the data model employed by the factory grid.

Factory grid 160 includes a data curation module 262, a patient matching module 264, an indexing module 266, and various calculation/analytic engines 268. Data curation module 262 performs data curation operations including mapping codes, data cleansing, and standardization, while patient matching module 264 performs patient matching operations to determine records associated with the same patient. Indexing module 266 performs indexing operations including combining records based on patient matching, mappings, and application of risk models. The calculation/analytic engines perform the desired analytics based on queries received from end-users from an interaction layer 230 enabling application server cluster 140 to provide various applications for processing and accessing the data (e.g., analytic applications, SQL access, etc.). The staging and factory grids form an aggregation and engines layer 220 to process the acquired data, while the queries are handled by factory grid 160 in conjunction with application server cluster 140 to produce desired results for the interaction layer.

The various applications of application server cluster 140 may be provided in a cloud environment. It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones or other devices, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly release to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

Figure 3:
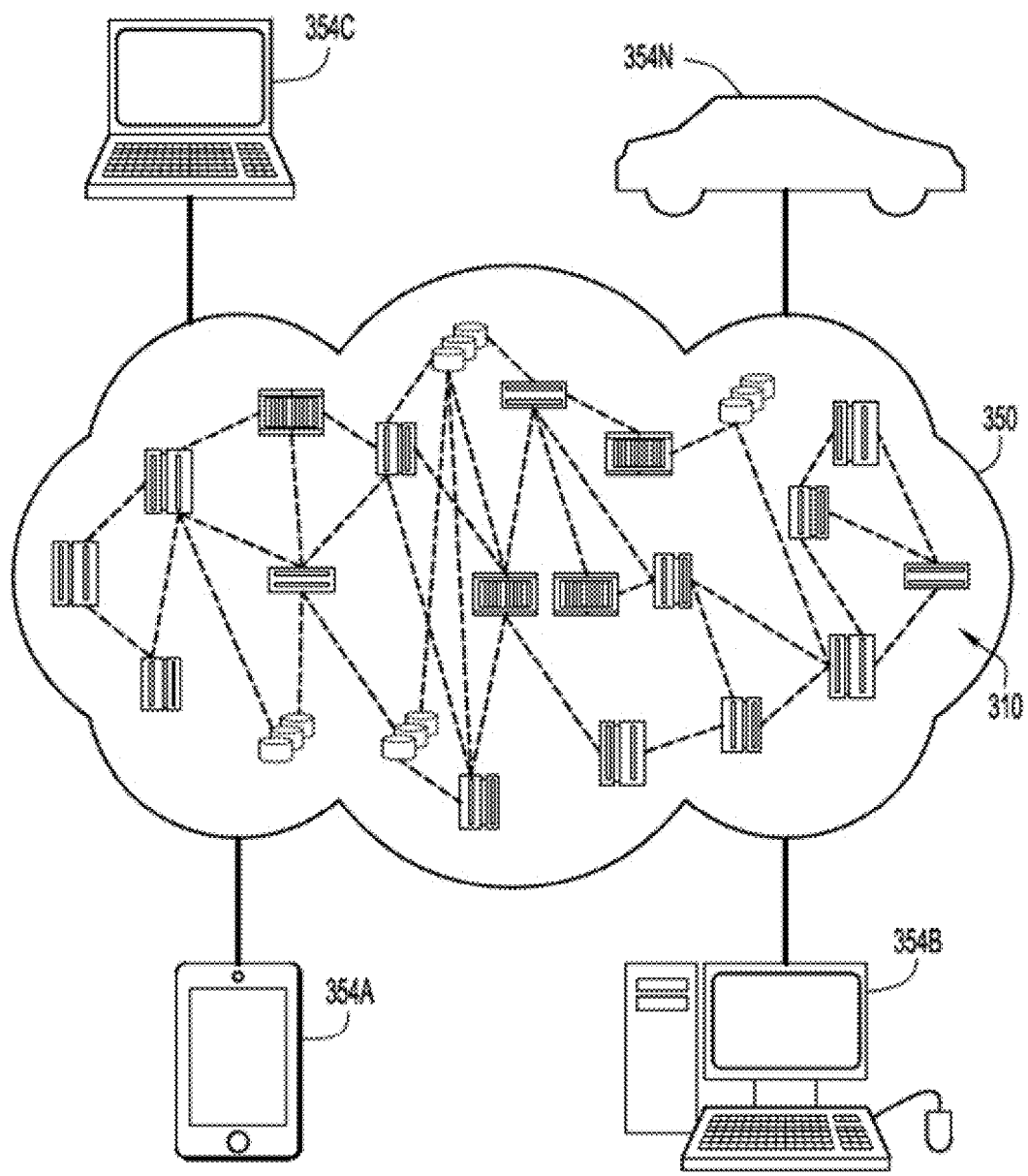
FIG. 3 is a diagrammatic illustration of an example cloud computing environment for the computing environment of FIG. 1 according to an embodiment of the present invention.

A cloud computing environment is service oriented with a focus on statelessness, low coupling, modularity, and semantic interoperability. At the heart of cloud computing is an infrastructure comprising a network of interconnected nodes. Referring now to FIG. 3, illustrative cloud computing environment 350 is depicted. As shown, cloud computing environment 350 comprises one or more cloud computing nodes 310 with which local computing devices used by cloud consumers, such as, for example, personal digital assistant (PDA) or cellular telephone 354A, desktop computer 354B, laptop computer 354C, and/or automobile computer system 354N may communicate. Nodes 310 may communicate with one another. They may be grouped (not shown) physically or virtually, in one or more networks, such as Private, Community, Public, or Hybrid clouds as described hereinabove, or a combination thereof. This allows cloud computing environment 350 to offer infrastructure, platforms and/or software as services for which a cloud consumer does not need to maintain resources on a local computing device. It is understood that the types of computing devices 354A-N shown in FIG. 3 are intended to be illustrative only and that computing nodes 310 and cloud computing environment 350 can communicate with any type of computerized device over any type of network and/or network addressable connection (e.g., using a web browser).

Figure 4:
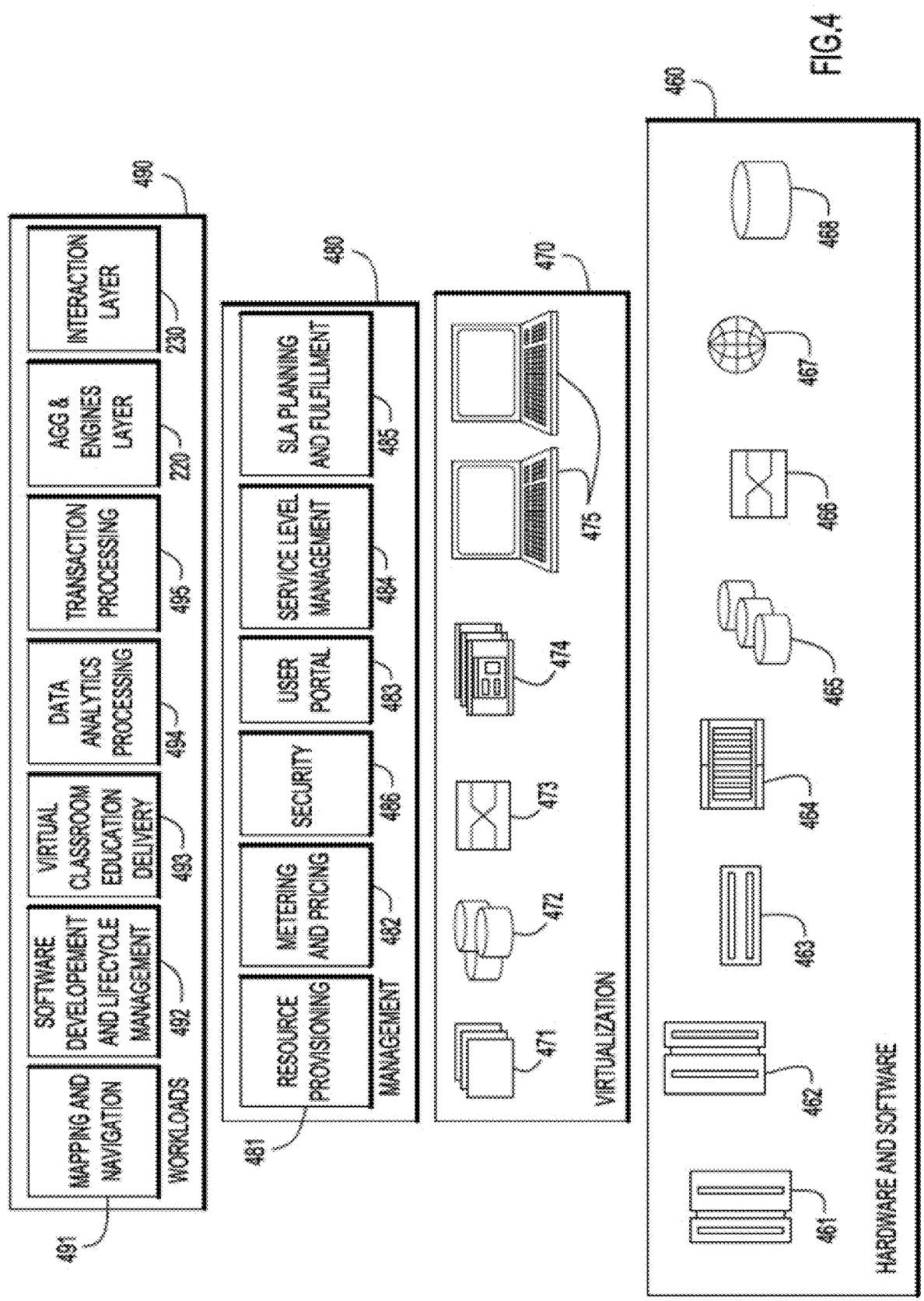
FIG. 4 is a diagrammatic illustration of abstraction model layers according to an embodiment of the present invention.

Referring now to FIG. 4, a set of functional abstraction layers provided by cloud computing environment 350 (FIG. 3) is shown. It should be understood in advance that the components, layers, and functions shown in FIG. 4 are intended to be illustrative only and embodiments of the invention are not limited thereto. As depicted, the following layers and corresponding functions are provided:

Hardware and software layer 460 includes hardware and software components. Examples of hardware components include: mainframes 461; RISC (Reduced Instruction Set Computer) architecture based servers 462; servers 463; blade servers 464; storage devices 465; and networks and networking components 466. In some embodiments, software components include network application server software 467 and database software 468.

Virtualization layer 470 provides an abstraction layer from which the following examples of virtual entities may be provided: virtual servers 471; virtual storage 472; virtual networks 473, including virtual private networks; virtual applications and operating systems 474; and virtual clients 475.

In one example embodiment, management layer 480 may provide some or all of the functions for data center 115 described herein. Resource provisioning 481 provides dynamic procurement of computing resources and other resources that are utilized to perform tasks within the cloud computing environment. Metering and Pricing 482 provide cost tracking as resources are utilized within the cloud computing environment, and billing or invoicing for consumption of these resources. In one example, these resources may comprise application software licenses. Security 486 provides identity verification for cloud consumers and tasks, as well as protection for data and other resources. User portal 483 provides access to the cloud computing environment for consumers and system administrators. Service level management 484 provides cloud computing resource allocation and management such that required service levels are met. Service Level Agreement (SLA) planning and fulfillment 485 provide pre-arrangement for, and procurement of, cloud computing resources for which a future requirement is anticipated in accordance with an SLA.

Workloads layer 490 provides examples of functionality for which the cloud computing environment may be utilized. Examples of workloads and functions which may be provided from this layer include: mapping and navigation 491; software development and lifecycle management 492; virtual classroom education delivery 493; data analytics processing 494; transaction processing 495; aggregation and engines layer 220 (FIG. 2); and interaction layer 230 (FIG. 2).

Figure 5:
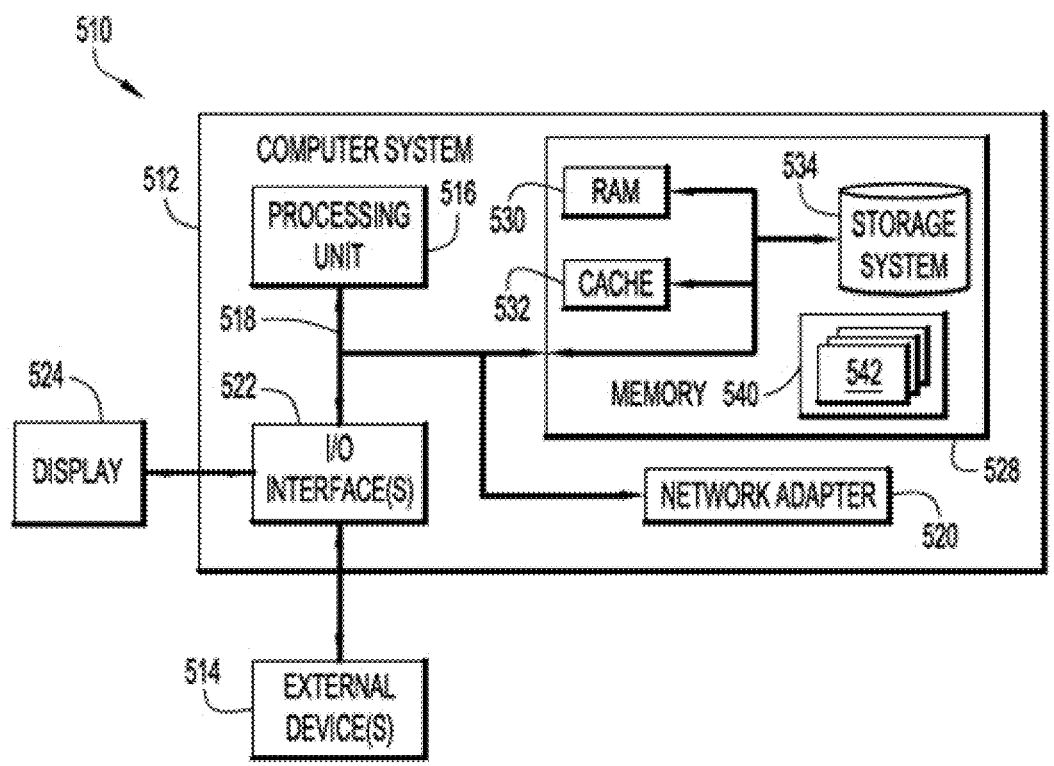
FIG. 5 is a block diagram of a computing node according to an embodiment of the present invention.

Referring now to FIG. 5, a schematic of an example of a computing node or device 510 of computer environment 100 (e.g., health data gateway 110, application server cluster 140, gateway controller 145, configuration processing device 147, computing nodes of staging grid 150, computing nodes of factory grids 160, etc.) and cloud environment 350 (e.g., cloud computing node 310, etc.) is shown. The computing node or device is only one example of a suitable computing node for computing environment 100 and cloud computing environment 350 and is not intended to suggest any limitation as to the scope of use or functionality of embodiments of the invention described herein. Regardless, computing node 510 is capable of being implemented and/or performing any of the functionality set forth herein.

In computing node 510, there is a computer system 512 which is operational with numerous other general purpose or special purpose computing system environments or configurations. Examples of well-known computing systems, environments, and/or configurations that may be suitable for use with computer system 512 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system 512 may be described in the general context of computer system executable instructions, such as program modules, being executed by a computer system. Generally, program modules may include routines, programs, objects, components, logic, data structures, and so on that perform particular tasks or implement particular abstract data types. Computer system 512 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 5, computer system 512 is shown in the form of a general-purpose computing device. The components of computer system 512 may include, but are not limited to, one or more processors or processing units 516, a system memory 528, and a bus 518 that couples various system components including system memory 528 to processor 516.

Bus 518 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system 512 typically includes a variety of computer system readable media. Such media may be any available media that is accessible by computer system 512, and it includes both volatile and non-volatile media, removable and non-removable media.

System memory 528 can include computer system readable media in the form of volatile memory, such as random access memory (RAM) 530 and/or cache memory 532. Computer system 512 may further include other removable/non-removable, volatile/non-volatile computer system storage media. By way of example only, storage system 534 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 518 by one or more data media interfaces. As will be further depicted and described below, memory 528 may include at least one program product having a set (e.g., at least one) of program modules that are configured to carry out the functions of embodiments of the invention.

Program/utility 540, having a set (at least one) of program modules 542, may be stored in memory 528 by way of example, and not limitation, as well as an operating system, one or more application programs, other program modules, and program data. Each of the operating system, one or more application programs, other program modules, and program data or some combination thereof, may include an implementation of a networking environment. Program modules 542 generally carry out the functions and/or methodologies of embodiments of the invention as described herein.

Computer system 512 may also communicate with one or more external devices 514 such as a keyboard, a pointing device, a display 524, etc.; one or more devices that enable a user to interact with computer system 512; and/or any devices (e.g., network card, modem, etc.) that enable computer system 512 to communicate with one or more other computing devices. Such communication can occur via Input/Output (I/O) interfaces 522. Still yet, computer system 512 can communicate with one or more networks such as a local area network (LAN), a general wide area network (WAN), and/or a public network (e.g., the Internet) via network adapter 520. As depicted, network adapter 520 communicates with the other components of computer system 512 via bus 518. It should be understood that although not shown, other hardware and/or software components could be used in conjunction with computer system 512. Examples, include, but are not limited to: microcode, device drivers, redundant processing units, external disk drive arrays, RAID systems, tape drives, and data archival storage systems, etc.

Figure 6:
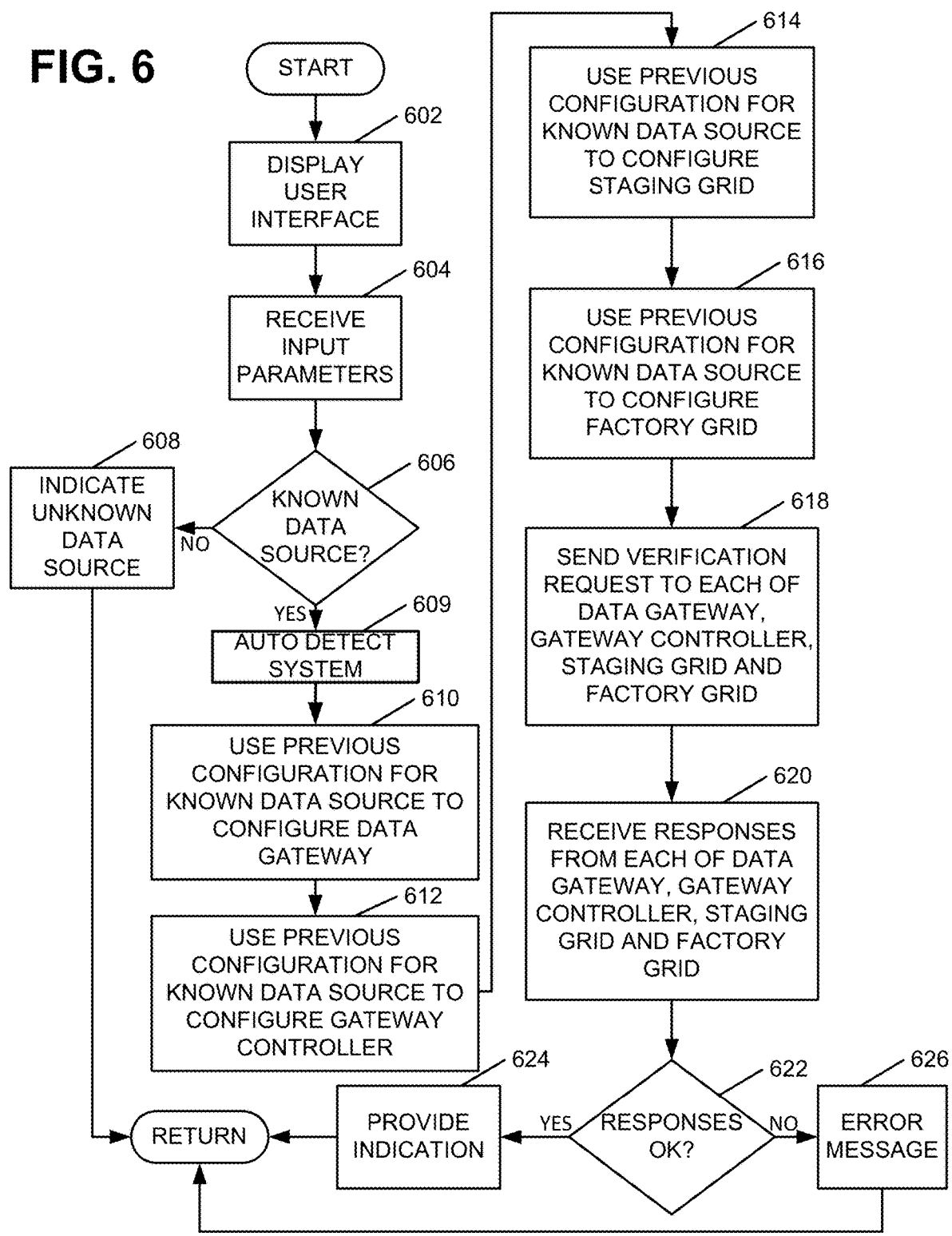
FIG. 6 is a flowchart of an example process that a configuration processing device may perform in various embodiments.

FIG. 6 is a flowchart explaining a process that may be implemented in some embodiments. The process may begin with configuration processing device 147 displaying, or presenting, a user interface to a user (act 602).

Figure 7:
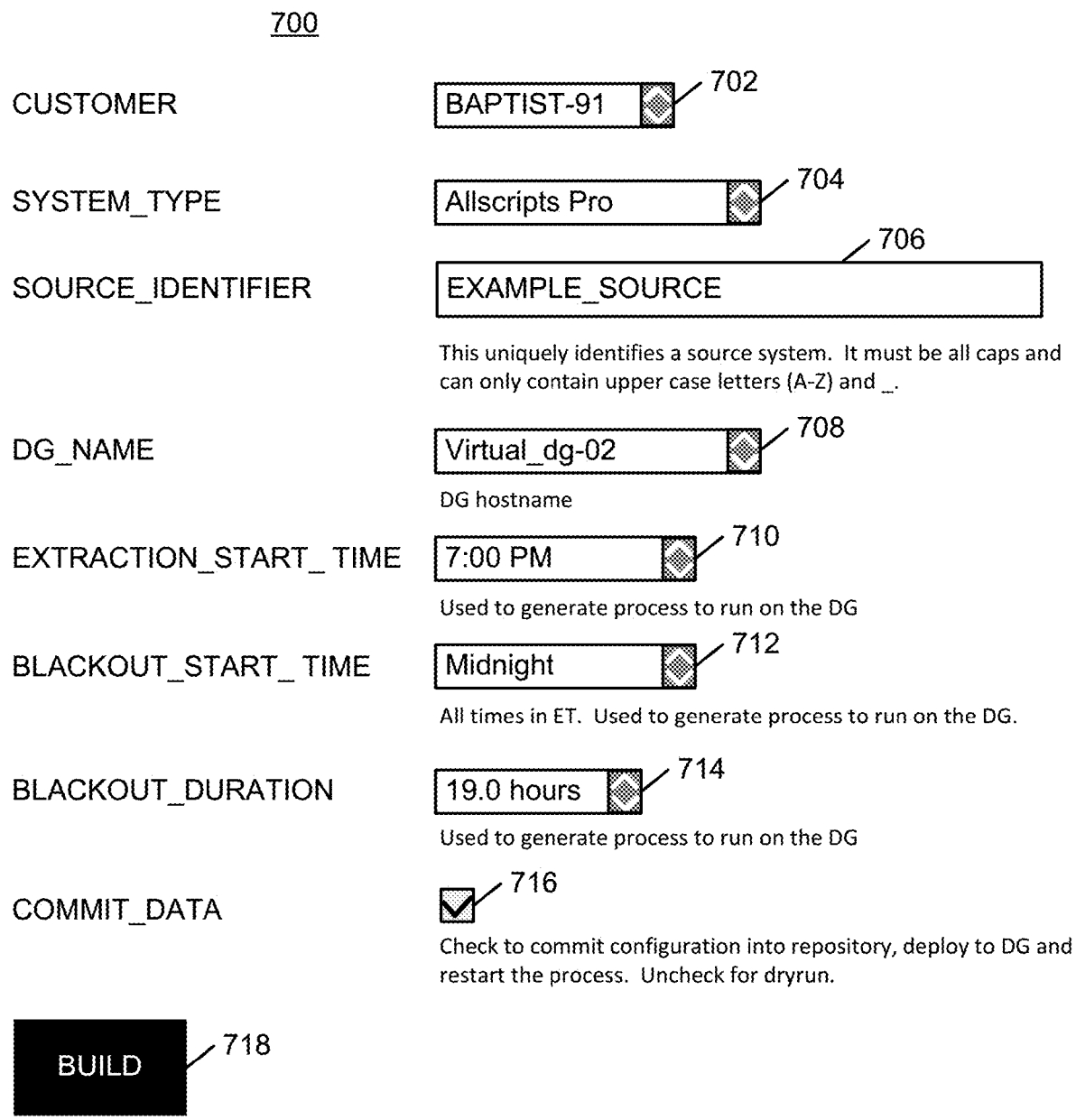
FIG. 7 illustrates an example user interface in which a user may enter parameters that may be used to determine whether a data source is known from a previous integration.

FIG. 7 illustrates an example user interface 700 for various embodiments. User interface 700 may include a customer name, which may be entered by selecting icon 702, thereby causing a list of customers to be displayed, from which a selection may be made. The user may enter a system type by selecting icon 704, thereby causing a list of system types to be displayed, from which a selection may be made. Alternatively, configuration processing device 147 may determine a system type if a source identifier is known from a previous configuration.

The user may enter a name of a data source, or source identifier, into input box 706. In one embodiment, the user may enter the source identifier using any of capital letters A-Z and "_". The user may enter a data gateway name by selecting icon 708, thereby causing a list of the data gateways to be displayed, from which a selection may be made. The user may enter an extraction start time (indicating when extraction processing may begin) by selecting icon 710, thereby causing a list of times to be displayed, from which a selection may be made. The user may enter a blackout start time, indicating a time at which extraction processing may not be performed, by selecting icon 712, thereby causing a list of blackout start times to be displayed, from which a selection may be made. The user may enter a blackout duration amount indicating a length of a blackout period by selecting icon 714, thereby causing a list of duration times to be displayed, from which a selection may be made. The user may select box 716 to indicate that the configuration is to be entered into a repository and deployed to data gateway 110 upon selection of BUILD button 718.

Returning to FIG. 6, configuration processing device 147 may receive input parameters from a user interface (act 604) and may determine whether the parameters indicate a known data source from a previous integration (act 606). A known data source may be determined when an indicated system type and source identifier are known from a previous integration. If the parameters do not indicate a known data source from a previous integration, then configuration processing device 147 may indicate that the data source is unknown by displaying a message to the user, making an announcement to the user, causing a particular alert sound to be made, or by other methods.

If the data source is known from a previous integration, then configuration processing device 147 may automatically detect a type of source system, in some embodiments (act 609). For example, to identify an Allscripts Pro system, configuration processing device 147 may run some ALLPRO queries and record a success or a failure.

When the data source is known a pattern pertaining to the source file is already known and configuration processing device 147 may obtain a previous configuration for the known data source from a repository and may send respective configuration information, based on the obtained previous configuration, to health data gateway 110 to configure health data gateway 110 (act 610).

Configuration processing device 147 may send respective configuration information, based on the obtained previous configuration, to gateway controller 145 to configure gateway controller 145 (act 612). Examples of what may be configured include, but are not limited to: a database system to connect to; a user name and password to use for the connection; a time at which extraction is to be performed; and a data pipeline for the extraction to follow (i.e. which message queuing system to use, name of the queue, and destination of the messages). Configuration processing device 147 may retrieve the configuration information from a source control repository. Configuration processing device 147 may interpret stored configuration values and may determine which devices and services on those devices are to be configured. Those devices may be configured based on values retrieved from the source control repository. The configuration information may configure gateway controller 145 to 1) forward incoming messages to a correct processing device, which may be another gateway controller) and 2) perform processing that stores the incoming data into staging grid 150.

Configuration processing device 147 may send respective configuration information, based on the obtained previous configuration, to staging grid 150 (act 614) and factory grid 160 to configure staging grid 150 and factory grid 160 (act 616). Configuration processing device 147 may send verification request messages to each of health data gateway 110, gateway controller 145, staging grid 150 and factory grid 160 (act 618). Respective agents (not shown) within health data gateway 110, gateway controller 145, staging grid 150 and factory grid 160 may receive the respective verification request messages, may determine whether any needed programs and configurations are missing, may deploy any needed programs and configurations, may validate an integrity of connections and hardware systems, and may send respective responses to configuration processing device 147 indicating respective statuses (act 620). The agents may compare the received configuration information to a current configuration to perform the verification. Configuration processing device 147 may then determine whether all of the responses indicate that the system is ready for an extraction, transformation and load process (act 622).

If the responses indicate that at least one of health data gateway 110, gateway controller 145, staging grid 150 and factory grid 160 are not ready for the extraction, transformation and load process, then configuration processing device 147 may indicate an error to the user by displaying or presenting an error message, indicating an error through an audio indication, or by other methods (act 626). Otherwise, configuration processing device 147 may provide a visual or audio indication indicating that the system is ready for extraction, transformation and load processing (act 624) and may initiate the extraction process in health data gateway 110. Processing by configuration processing device 147 may then be completed.

FIG. 8 shows an example of an input configuration file that would define a previously known source system. A template such as this could be used by configuration processing device 147 to configure the extraction of data from a known source system with little to no intervention from a user. For systems having source files which have previously been integrated, the input configuration file can easily be created and automatically generated as well when the data source is known. Configuration processing device 147 may use the input configuration to decide how to configure publishers in a staging relational database management system as well as extractors on health data gateway 110.

In an industry in which many customers use products such as relational database systems from a same set of vendors, onboarding of customers can be performed extremely fast using embodiments of the invention. Embodiments of the invention would be useful in industries, including, but not limited to, healthcare, business intelligence and other markets related to providing reports regarding data stored in various forms, including, but not limited to, relational databases, flat files, and other standard message formats.

It will be appreciated that the embodiments described above and illustrated in the drawings represent only a few of the many ways of implementing embodiments for automating configuration of a system for data extraction.

The environment of the present invention embodiments may include any number of computer or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., browser software, communications software, server software, etc.). These systems may include any types of monitors and input devices (e.g., keyboard, mouse, voice recognition, etc.) to enter and/or view information.

It is to be understood that the software of the present invention embodiments may be implemented in any desired computer language and could be developed by one of ordinary skill in the computer arts based on the functional descriptions contained in the specification and flow charts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flow charts may be modified in any manner that accomplishes the functions described herein. In addition, the functions in the flow charts or description may be performed in any order that accomplishes a desired operation.

The software of the present invention embodiments may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information. The database system may be implemented by any number of any conventional or other databases, data stores or storage structures (e.g., files, databases, data structures, data or other repositories, etc.) to store information. The database system may be included within or coupled to the server and/or client systems. The database systems and/or storage structures may be remote from or local to the computer or other processing systems, and may store any desired data.

The present invention embodiments may employ any number of any type of user interface (e.g., Graphical User Interface (GUI), command-line, prompt, etc.) for obtaining or providing information, where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

The report may include any information arranged in any fashion, and may be configurable based on rules or other criteria to provide desired information to a user.

The present invention embodiments are not limited to the specific tasks or algorithms described above, but may be utilized for networks other than healthcare networks. For example, various embodiments may be applied to a data gateway, instead of a health data gateway. Factory grid 160 may include an individual matching module, instead of a patient matching module.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Further, although the drawings and text refer to a healthcare network and a health data gateway, embodiments of the invention may be applied to other than healthcare networks. In addition, embodiments may employ a data gateway, instead of a health data gateway. Factory grid 160 may include an individual matching module, instead of a patient matching module, which matches records to individuals.

We claim as our invention:

1. A computer program product comprising:
   at least one computer readable storage medium having computer readable program code embodied therewith for execution on a processing system to configure a plurality of processing devices in a data pipeline, the computer readable program code is configured to be executed by the processing system to:
   determine that a data source is a known data source based on parameters indicating that the data source is the known data source from a previous integration for the data source, wherein the data source includes stored electronic data, and the parameters include a source identifier, which uniquely identifies a source system, and a system type; and
   automatically perform, when the data source is determined to be the known data source:
   retrieve configuration information from the previous integration for the known data source;
   interpret configuration values included in the retrieved configuration information and determine devices in the data pipeline and services on the devices to configure based on the configuration information for the known data source;
   send first configuration information based on the retrieved configuration information to a data gateway in a network to configure the data gateway to acquire data from the known data source having a connection with the data gateway and transmit the acquired data to a gateway controller;
   send second configuration information based on the retrieved configuration information to the gateway controller to configure the gateway controller to receive the acquired data transmitted from the data gateway and perform processing of the acquired data to produce first processed data that is stored to a first data system with a first data model;
   send third configuration information based on the retrieved configuration information to the first data system to configure the first data system to process the first processed data to produce second processed data that is published to a second data system with a second data model;
   send fourth configuration information based on the retrieved configuration information to the second data system to configure the second data system to receive the published second processed data;
   send respective verification request messages to each of the data gateway, the gateway controller, the first data system, and the second data system, receipt of the respective verification request messages causing respective agents within each of the data gateway, the gateway controller, the first data system, and the second data system to deploy any missing programs and configurations, validate an integrity of connections and hardware systems, and send respective responses to the processing system;

receive the respective responses indicating respective statuses of each of the data gateway, the gateway controller, the first data system, and the second data system; and responsive to determining that the received respective responses from the each of the data gateway, the gateway controller, the first data system, and the second data system indicate readiness for extraction, transformation and load processing:

provide an indication of the readiness for the extraction, transformation and load processing, and initiate an extraction process in the data gateway to extract data from the known data source and transmit the extracted data to the gateway controller, wherein:

the extracted data is processed by the gateway controller to produce the first processed data that is stored to the first data system in accordance with the first data model employed by the first data system, and the first processed data is processed by the first data system to produce second processed data that is published to the second data system in accordance with the second data model.

2. The computer program product of claim 1, wherein the source identifier and information related to an address of the data source are received from a user via a user interface of a processing device.

3. The computer program product of claim 1, wherein the second configuration information configures the gateway controller to process the extracted data to a staging grid employing the first data model of a system of the data source.

4. The computer program product of claim 3, wherein the third configuration information further configures the staging grid to structurally prepare and transform the first processed data in the staging grid to produce the second processed data and publish the second processed data to a factory grid.

5. The computer program product of claim 4, wherein the fourth configuration information configures the factory grid to perform data curation, matching of individuals associated with the published second processed data, and indexing.

6. The computer program product of claim 1, wherein the computer readable program code further configures the processing system to validate that each of the data gateway, the gateway controller, the first data system and the second data system is properly configured.

7. The computer program product of claim 1, wherein the computer readable program code further configures the processing system to:

determine based on respective parameters pertaining to each corresponding data source of a plurality of data sources, whether the each corresponding data source is a respective known data source, wherein the plurality of data sources include stored electronic data, and the respective parameters pertaining to the each corresponding data source include a respective source identifier, which uniquely identifies a respective source system, and a respective system type;

perform, when the plurality of data sources are determined to be the known data sources:

send to a plurality of processing devices respective configuration information associated with each of the plurality of data sources, the respective configuration information being based on configuration information from a respective previous integration for each of the known data sources; and configure the plurality of processing devices as an operational data pipeline, based on the configuration information, to:

extract data from the known data sources to the first data system, transform the extracted data to the second data model employed by the second data system, and load the transformed data into the second data system.

8. A processing device comprising:

a communication interface;

at least one processor;

a memory; and a communication bus connecting the at least one processor with the memory and the communication interface, wherein the memory includes instructions for the at least one processor such that, when the instructions are loaded and executed by the at least one processor, the processing device performs a method to configure a plurality of processing devices in a data pipeline, the method comprising:

determining that a data source is a known data source based on parameters indicating that the data source is the known data source from a previous integration for the data source, wherein the data source includes stored electronic data, and the parameters include a source identifier, which uniquely identifies a source system, and a system type; and automatically performing, when the data source is determined to be the known data source:

retrieving configuration information from the previous integration for the known data source;

interpreting configuration values included in the retrieved configuration information and determining devices in the data pipeline and services on the devices to configure based on the configuration information for the known data source;

sending first configuration information based on the retrieved configuration information to a data gateway in a network to configure the data gateway to acquire data from the known data source having a connection with the data gateway and transmit the acquired data to a gateway controller;

sending second configuration information based on the retrieved configuration information to the gateway controller to configure the gateway controller to receive the acquired data transmitted from the data gateway and perform processing of the acquired data to produce first processed data that is stored to a first data system with a first data model;

sending third configuration information based on the retrieved configuration information to the first data system to configure the first data system to process the first processed data to produce second processed data that is published to a second data system with a second data model;

sending fourth configuration information based on the retrieved configuration information to the second data system to configure the second data system to receive the published second processed data;

sending respective verification request messages to each of the data gateway, the gateway controller, the first data system, and the second data system, receipt of the respective verification request messages causing respective agents within each of the data gateway, the gateway controller, the first data system, and the second data system to deploy any missing programs and configurations, validate an integrity of connections and hardware systems, and send respective responses;

receiving the respective responses indicating respective statuses of each of the data gateway, the gateway controller, the first data system, and the second data system; and responsive to determining that the received respective responses from the each of the data gateway, the gateway controller, the first data system, and the second data system indicate readiness for extraction, transformation and load processing:
provic an indication of the readiness for the extraction, transformation and load processing, and
initiating an extraction process in the data gateway to extract data from the known data source and transmit the extracted data to the gateway controller, wherein:
the extracted data is processed by the gateway controller to produce the first processed data that is stored to the first data system in accordance with the first data model employed by the first data system, and
the first processed data is processed by the first data system to produce second processed data that is published to the second data system in accordance with the second data model.

9. The processing device of claim 8, wherein the third configuration information further configures a staging grid to structurally prepare and transform the first processed data in the staging grid to produce the second processed data and publish the second processed data to a factory grid.

10. The processing device of claim 8 and, wherein the fourth configuration information further configures a factory grid to perform data curation, matching of individuals associated with the published second processed data, and indexing.

11. The processing device claim 8, wherein the method further comprises:
communicating with the data gateway, the gateway controller, a staging grid and a factory grid to determine whether each of the data gateway, the gateway controller, the staging grid and the factory grid is properly configured.

12. The processing device of claim 11, wherein the staging grid and the factory grid are Hadoop clusters.

13. The processing device of claim 8, wherein the method further comprises:
determining, based on respective parameters pertaining to each corresponding data source of a plurality of data sources, whether the each corresponding data source is a respective known data source, wherein the plurality of data sources include stored electronic data, and the respective parameters pertaining to the each corresponding data source include a respective source identifier, which uniquely identifies a respective source system, and a respective system type;
performing, when the plurality of data sources are determined to be the known data sources:
sending, to a plurality of processing devices, respective configuration information associated with each of the plurality of data sources, the respective configuration information being based on configuration information from a respective previous integration for each of the known data sources; and
configuring the plurality of processing devices as an operational data pipeline, based on the configuration information, to:
extract data from the known data sources to the first data system,
transform the extracted data to the second data model employed by the second data system, and
load the transformed data into the second data system.

* * * * *